US010221019B2

(12) United States Patent
Hou et al.

(10) Patent No.: US 10,221,019 B2
(45) Date of Patent: Mar. 5, 2019

(54) METHOD OF RECOGNIZING CONVEYOR BELT WEAR CONDITION

(71) Applicant: The Yokohama Rubber Co., LTD., Minato-ku, Tokyo (JP)

(72) Inventors: Gang Hou, Hiratsuka (JP); Deqing Zou, Hiratsuka (JP); Kazunori Ono, Hiratsuka (JP); Sakiko Kono, Hiratsuka (JP)

(73) Assignee: The Yokohama Rubber Co., LTD. (JP)

(*) Notice: Subject to any disclaimer, the term of this patent is extended or adjusted under 35 U.S.C. 154(b) by 0 days.

(21) Appl. No.: 15/745,079

(22) PCT Filed: May 13, 2016

(86) PCT No.: PCT/JP2016/064286
§ 371 (c)(1),
(2) Date: Jan. 15, 2018

(87) PCT Pub. No.: WO2017/051566
PCT Pub. Date: Mar. 30, 2017

(65) Prior Publication Data
US 2018/0208402 A1 Jul. 26, 2018

(30) Foreign Application Priority Data
Sep. 24, 2015 (JP) .................. 2015-186889

(51) Int. Cl.
B65G 43/02 (2006.01)
B65G 43/00 (2006.01)
G01N 3/56 (2006.01)

(52) U.S. Cl.
CPC ............. *B65G 43/02* (2013.01); *G01N 3/56* (2013.01); *B65G 2203/0275* (2013.01); *B65G 2207/48* (2013.01)

(58) Field of Classification Search
None
See application file for complete search history.

(56) References Cited

U.S. PATENT DOCUMENTS 8,618,929 B2 * 12/2013 Ganapathy ............. B65G 43/02
340/539.1
8,844,713 B2 * 9/2014 Lasecki ................ B65G 17/064
198/851

(Continued)

FOREIGN PATENT DOCUMENTS

| JP | 2004-020319 | 1/2004 |
| WO | WO 2013/053013 | 4/2013 |
| WO | WO 2013/179903 | 12/2013 |

OTHER PUBLICATIONS

International Search Report for International Application No. PCT/JP2016/064286 dated Jun. 21, 2016, 2 pages, Japan.

*Primary Examiner* — Kavel Singh
(74) *Attorney, Agent, or Firm* — Thorpe North & Western

(57) ABSTRACT

A method of recognizing a conveyor belt wear condition is provided. Relationships between an apparent compressive stress in a wear resistance test and surface roughness of a sample and between the surface roughness and amount of wear per unit frictional energy of the sample are acquired. A wear condition of an upper cover rubber is recognized based on an apparent compressive stress generated on the upper cover rubber at a use site, and a database is created based on the relationships. Alternatively, relationships between an average wear pitch calculated from the surface roughness and viscoelastic properties of the sample and between the average wear pitch and an actual amount of wear of the sample are acquired. A wear condition of the upper cover rubber is recognized based on the viscoelastic properties of the upper cover rubber of the use site and a database is created based on the relationships.

3 Claims, 7 Drawing Sheets

(56) References Cited

U.S. PATENT DOCUMENTS

| | | | | |
|---|---|---|---|---|
| 9,284,129 B2* | 3/2016 | Sakaguchi | ............ | B65G 43/02 |
| 2008/0257692 A1* | 10/2008 | Wallace | ................ | B65G 43/02 |
| | | | | 198/810.02 |
| 2015/0170109 A1 | 6/2015 | Sakuragi | | |

* cited by examiner

METHOD OF RECOGNIZING CONVEYOR BELT WEAR CONDITION

TECHNICAL FIELD

The present technology relates to a method of recognizing a conveyor belt wear condition, and particularly relates to a method of recognizing a conveyor belt wear condition where a wear condition of an upper cover rubber at a conveyor belt use site can be accurately recognized based on the results of a wear resistance evaluation test using a sample.

BACKGROUND ART

Various objects including iron ore, limestone, and other mineral resources are conveyed by conveyor belts. When being conveyed by the conveyor belt, an object to be conveyed is fed onto an upper cover rubber of the conveyor belt from a hopper or another conveyor belt. The fed object to be conveyed is loaded on the upper cover rubber and conveyed in a traveling direction of the conveyor belt. When the object to be conveyed is loaded on the upper cover rubber and conveyed, the upper cover rubber is subject to wear as a result of the object to be conveyed sliding on the upper cover rubber. The amount of wear generated on the upper cover rubber due to the fed object to be conveyed greatly changes based on the specification and use conditions of the conveyor belt.

Evaluation methods using a Pico abrasion test, DIN (German Institute for Standardization) abrasion test, Lambourn abrasion test, Taber abrasion test, Williams abrasion test, Akron abrasion test, or the like are known as methods of evaluating rubber wear resistance. Furthermore, evaluation methods using a wear testing device for a conveyor belt was also proposed (for example, refer to Japanese Unexamined Patent Application Publication No. 2004-20319). With these evaluation methods, the amount of wear of a worn rubber sample is measured by pressing a pressing body against a rubber sample while relatively moving both. However, the wear resistance obtained by these conventional evaluation methods and actual wear resistance of a conveyor belt at a use site greatly deviate. Therefore, evaluation methods using a rubber sample have a problem where a wear condition of a conveyor belt at a use site can not be accurately recognized.

SUMMARY

The present technology provides a method of recognizing a conveyor belt wear condition where a wear condition of an upper cover rubber at a use site can be accurately recognized based on the results of a wear resistance evaluation test using a sample.

A method of recognizing a conveyor belt wear condition according to the present technology includes the steps of: performing a rubber wear resistance test using a sample for each rubber type, by varying apparent compressive stress generated by a pressing force applied to the sample; acquiring a relationship between the apparent compressive stress and a surface roughness of the sample obtained from the test; acquiring a relationship between the surface roughness and an amount of wear per unit frictional energy of the sample obtained by the test; creating a database showing a correlation between the surface roughness, the apparent compressive stress, and the amount of wear per unit frictional energy based on the acquired relationships; and recognizing a wear condition of an upper cover rubber at a conveyor belt use site, based on the database and apparent compressive stress generated by a pressing force provided by an object to be conveyed with regard to the upper cover rubber.

Another method of recognizing a conveyor belt wear condition according to the present technology includes the steps of: performing a rubber wear resistance test using a sample for a plurality of rubber types with different viscoelastic properties; acquiring a relationship between an average wear pitch calculated from a surface roughness of the sample obtained by the test and viscoelastic properties of the rubber type of the sample; acquiring a relationship between the average wear pitch and an actual amount of wear of the sample obtained by the test; creating a database showing a correlation between the average wear pitch, the viscoelastic properties, and the actual amount of wear of the sample; and recognizing a wear condition of the upper cover rubber based on the database, the average wear pitch of an upper cover rubber of a conveyor belt, and viscoelastic properties of the rubber type of the upper cover rubber.

With the present technology, an actual wear condition of an upper cover rubber of a conveyor belt is recognized based on the results of a rubber wear resistance evaluation test of using a sample. At this time, attention is given to rubber surface roughness generated due to wear.

In rubber subject to friction, a correlation between rubber surface roughness and apparent compressive stress generated by a pressing force provided on the rubber is high, and a correlation between rubber surface roughness and amount of wear per unit frictional energy of rubber subject to friction is high. Therefore, a correlation between apparent compressive stress and amount of wear per unit frictional energy is also high. Therefore, with the former method of recognizing a conveyor belt wear condition according to the present technology, a wear condition of an upper cover rubber at a use site can be accurately recognized based on a database showing a correlation between the surface roughness, the apparent compressive stress, and the amount of wear per unit frictional energy, and based on the apparent compressive stress generated on the upper cover rubber cover at a conveyor belt use site.

Furthermore, in rubber subject to friction, a correlation between viscoelastic properties of the rubber and average wear pitch calculated from the rubber surface roughness is high, and a correlation between an actual amount of wear of rubber and average wear pitch is high. Therefore, a correlation between viscoelastic properties of the rubber and actual amount of wear is also high. Therefore, with the latter method of recognizing a conveyor belt wear condition according to the present technology, a wear condition of an upper cover rubber at a use site can be accurately recognized based on a database showing a correlation between the average wear pitch, the viscoelastic properties, and the actual amount of wear, and based on the viscoelastic properties of the upper cover rubber of the conveyor belt, and based on an average wear pitch of the upper rubber cover.

DETAILED DESCRIPTION

Figure 1:
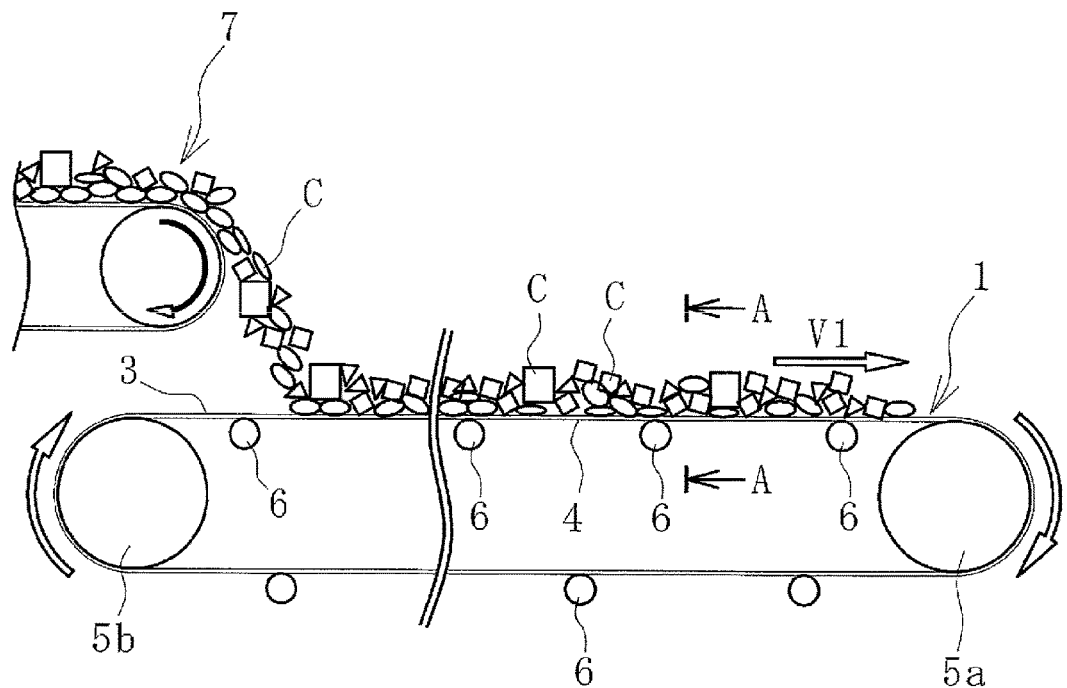
FIG. 1 is an explanatory diagram illustrating a conveyor belt line in a simplified manner.

A method of recognizing a conveyor belt wear condition according to the present technology will be described below based on embodiments illustrated in the drawings.

In a conveyor belt line illustrated in FIG. 1, an object to be conveyed C conveyed by another conveyor belt 7 is fed onto a conveyor belt 1 and conveyed to a conveying destination by the conveyor belt 1. The object to be conveyed C may be fed onto the conveyor belt 1 by a hopper or the like. The conveyor belt 1 is stretched at a predetermined tension between pulleys 5a and 5b.

Figure 2:
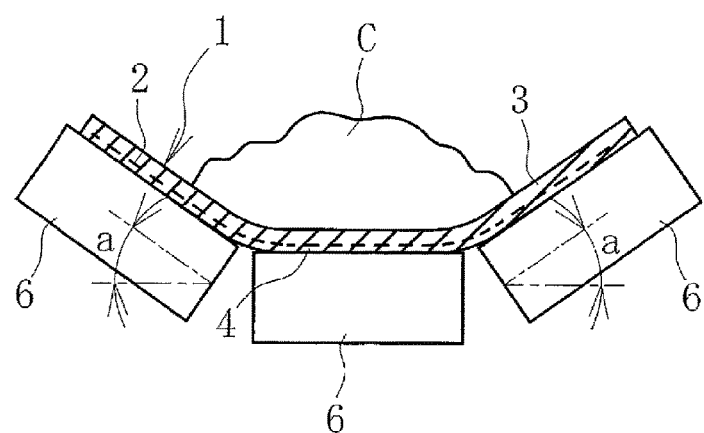
FIG. 2 is a cross-sectional view taken along A-A of FIG. 1.

As illustrated in FIG. 2, the conveyor belt 1 is configured from: a core layer 2 formed from a core as canvas, steel cord, or the like; and an upper cover rubber 3 and a lower cover rubber 4 that sandwich the core layer 2. The core layer 2 is a member bearing a tension that stretches the conveyor belt 1. The lower cover rubber 4 is supported by a support roller 6 on a carrier side of the conveyor belt 1, and the upper cover rubber 3 is supported in a flat shape by the support roller 6 on a return side of the conveyor belt 1. Three of the support rollers 6 are arranged on the carrier side of the conveyor belt 1 in a belt width direction. The conveyor belt 1 is supported by the support rollers 6 in a concave shape having a predetermined trough angle a. When the pulley 5a on a drive side is rotationally driven, the conveyor belt 1 is operated in one direction at a predetermined traveling speed V1. The object to be conveyed C is fed onto the upper cover rubber 3, loaded on the upper cover rubber 3, and then conveyed.

Figure 3:
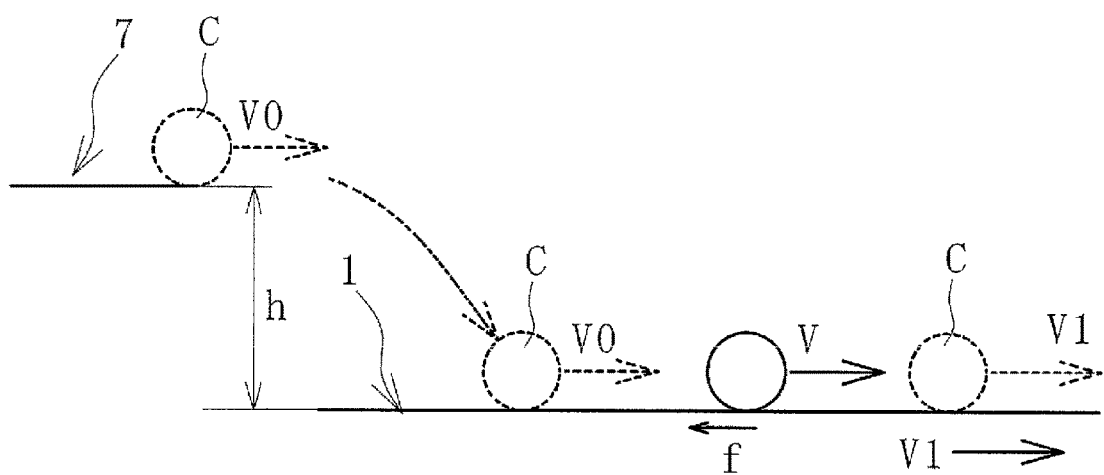
FIG. 3 is an explanatory diagram illustrating a friction force applied on a conveyor belt.

In the conveyor belt line, as illustrated in FIG. 3, the conveyor belt 1 and the other conveyor belt 7 are arranged at a vertical difference h (difference h in height positions of conveying surfaces of the conveyor belts). The object to be conveyed C is conveyed at a speed V0 (V0<V1) in a horizontal direction on the other conveyor belt 7. At the moment that the object to be conveyed C is loaded on the conveyor belt 1 from the other conveyor belt 7, the object to be conveyed C remains at the speed V0 in a horizontal direction, but is conveyed by the conveyor belt 1, and therefore, the speed in the horizontal direction thereof gradually reaches the same speed V1 as the traveling speed of the conveyor belt 1.

In other words, the object to be conveyed C contacting the upper cover rubber 3 moves at a relative moving speed V (=V1−V0) in a traveling direction with regard to the conveyor belt 1 while generating a compressive stress Pr on the upper cover rubber 3, and the final relative moving speed V is zero. During this time, a friction force f acts on the upper cover rubber 3, and the upper cover rubber 3 primarily wears due to this behavior of the object to be conveyed C.

The apparent compressive stress Pr generated on the upper cover rubber 3 by the object to be conveyed C is a pressing force (can be regarded as weight W of the object to be conveyed C) where the object to be conveyed C presses the upper cover rubber 3 with regard to a contact area Ar between the object to be conveyed C and the upper cover rubber 3. In other words, apparent compressive stress Pr=weight W of object to be conveyed C/contact area Ar.

Figure 4:
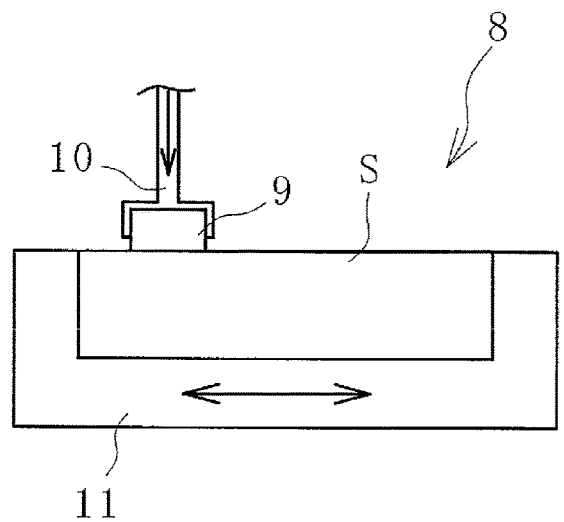
FIG. 4 is an explanatory diagram illustrating a basic structure of a wear testing device.

As illustrated in FIG. 4, a rubber wear testing device 8 is generally provided with a pressing body 9, a pressing mechanism 10 that presses the pressing body 9 against a rubber sample S, and a relative movement mechanism 11 that relatively moves the pressing body 9 and sample S. With a wear resistance testing method using the testing device 8, wear is generated on the sample S by relatively moving the pressing body 9 while pressing against the sample S to recognize the amount of wear and wear mode. Furthermore, with the aforementioned conventional wear testing method, the specifications of the pressing body 9, pressing mechanism 10, and relative movement mechanism 11 are all different.

With the present technology, a conventional wear resistance test is conducted using the sample S to acquire data. A Pico abrasion test, DIN abrasion test, Lambourn abrasion test, Taber abrasion test, Williams abrasion test, Akron abrasion test, or the like can be used as the conventional wear resistance test. Furthermore, a system 12 illustrated in FIG. 5, for example, is used to recognize a wear condition of the conveyor belt. The system 12 is provided with a calculation device 13 where a database D1, D2 created based on data acquired by a test is stored, an input unit 14 that inputs data into the calculation device 13, and a display unit 15 that displays calculation results based on the calculation device 13.

Figure 6:
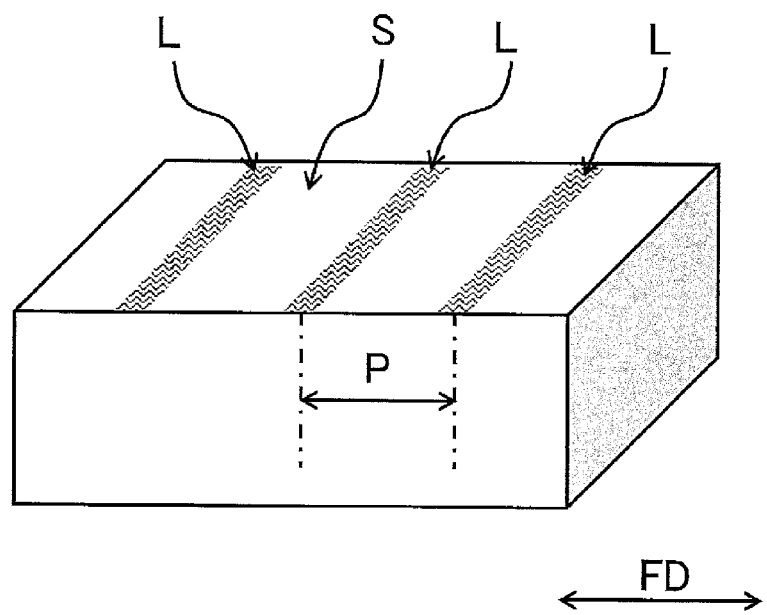
FIG. 6 is an explanatory diagram illustrating a wear line formed on a surface of a sample.
Figure 7:
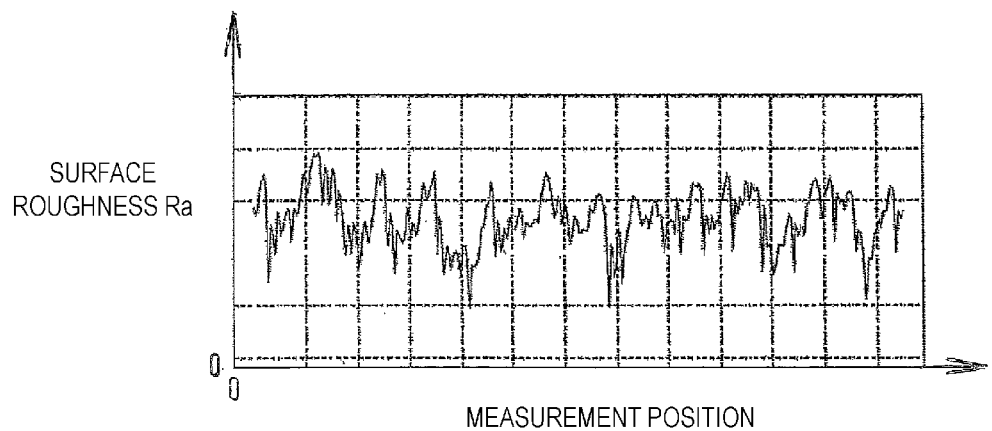
FIG. 7 is a graph showing a surface roughness of a sample.

In order to create the database D1, a conventional wear resistance test is conducted using the sample S on a plurality of rubber types. During the test, an apparent compressive stress Pe generated by a pressing force provided on the sample S is varied, and a relationship between the apparent compressive stress Pe and a surface roughness R of the sample S obtained by the test is acquired. A wear line L is formed on a surface of the samples S based on the test at intervals in a friction direction FD as illustrated in FIG. 6. The surface roughness R of the sample S is as shown in FIG. 7. In FIG. 7, an arithmetic mean roughness Ra as specified in JIS (Japanese Industrial Standards) is used as the surface roughness R. The surface roughness R can also be a maximum height (Ry), ten-point mean roughness (Rz), or the like in addition to the arithmetic mean roughness Ra.

Conventional wear resistance tests have varying apparent compressive stresses Pe generated on the sample S, and therefore, if a plurality of different conventional wear resistance tests are conducted, a wear resistance test is conducted by varying the apparent compressive stress Pe. For example, the apparent compressive stress Pe is 0.05 N/mm$^2$, 138.5 N/mm$^2$, and 0.333 N/mm$^2$ in a DIN abrasion test, Pico abrasion test, and Lambourn abrasion test, respectively. At least one of the DIN abrasion test or Pico abrasion test is preferably used as the wear resistance test.

Figure 8:
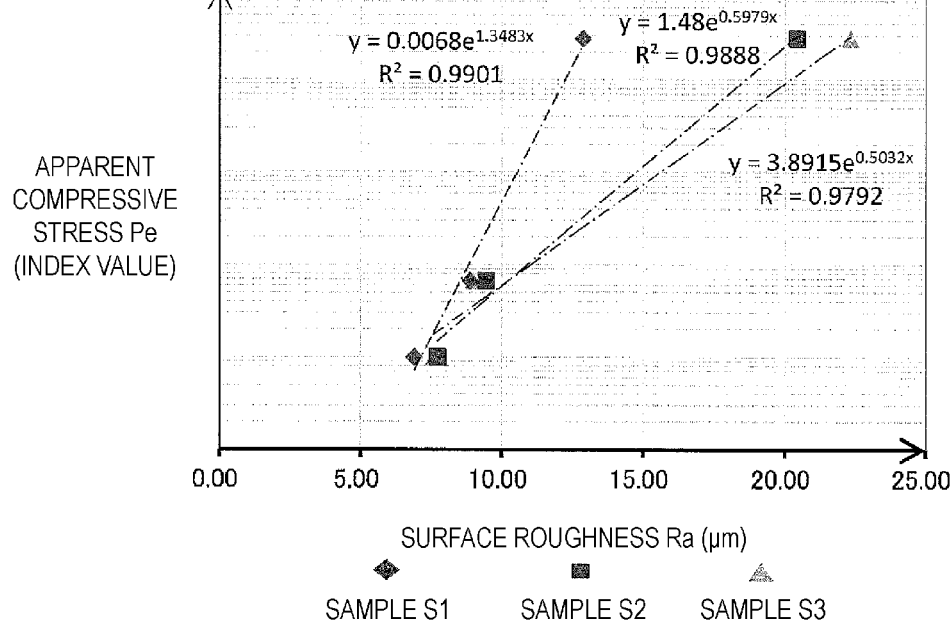
FIG. 8 is a graph showing a relationship between surface roughness and apparent compressive stress generated on a sample.

The acquired relationship between the apparent compressive stress Pe and surface roughness R has a high correlation as shown in FIG. 8. FIG. 8 is a semilogarithm graph, and data obtained by performing three different types of wear resistance tests using three types of samples S1, S2, and S3 with different types of rubber are shown. In FIG. 8, the apparent compressive stress Pe on a vertical axis is indicated by an index value, and as the index value increases, the apparent compressive stress Pe increases. As the apparent compressive stress Pe increases as shown in FIG. 8, the surface roughness R (surface roughness Ra in FIG. 8) increases.

A relationship between the surface roughness R and an amount of wear K1 per unit frictional energy of the sample S acquired by the test is further acquired by a conventional wear resistance test. The amount of wear K1 is calculated based on an actual amount of wear Vr of the sample S/(contact area between the sample S and pressing body 9×rubber tensile strength TB of the sample S×friction distance).

Figure 9:
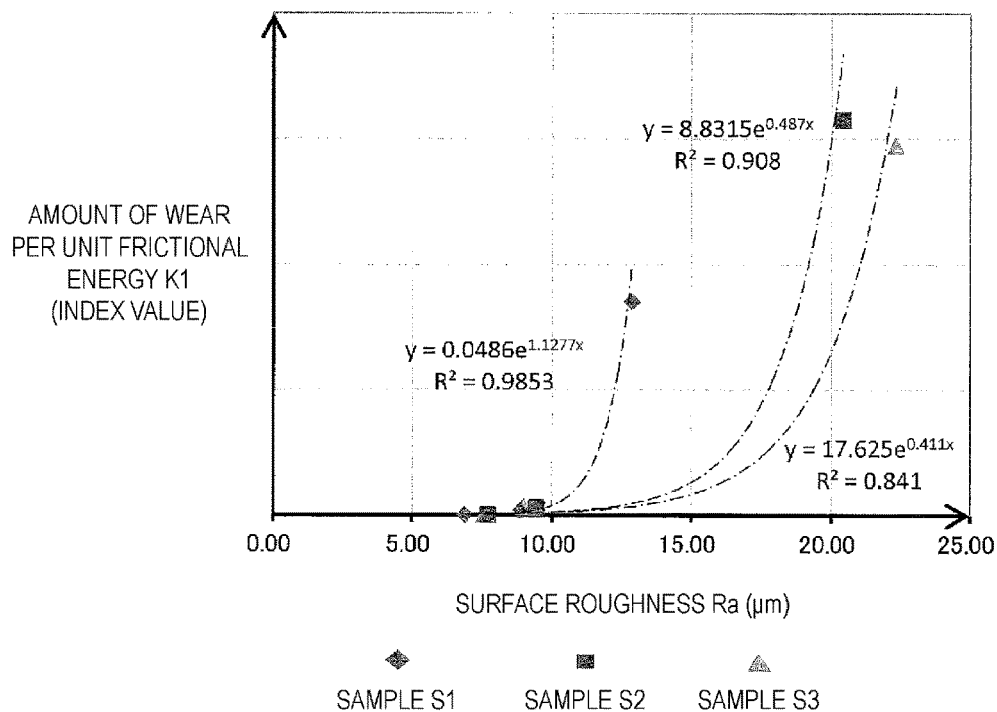
FIG. 9 is a graph showing a relationship between an amount of wear per unit frictional energy and surface roughness of a sample.

The acquired relationship between the surface roughness R and amount of wear K1 has a high correlation as shown in FIG. 9. In FIG. 9, the amount of wear K1 on a vertical axis is indicated by an index value, and as the index value increases, the amount of wear K1 increases. In other words, as the surface roughness R increases, the amount of wear K1 increases. In FIG. 9, the amount of wear K1 is used, but an amount of unit contact area wear K2 can be used instead. The amount of unit contact area wear K2 is calculated based on the actual amount of wear Vr of the sample S/(contact area between the sample S and pressing body 9). The acquired relationship between the surface roughness R and amount of wear K2 also has a high correlation similar to the acquired relationship between the surface roughness R and amount of wear K1.

A relationship between the apparent compressive stress Pe and amount of wear K1 can be acquired based on the relationships shown in FIG. 8 and FIG. 9 acquired by the test. The relationship between the apparent compressive stress Pe and amount of wear K1 also has a high correlation as shown in the semilogarithm graph of FIG. 10. In other words, as the apparent compressive stress Pe increases, the amount of wear K1 increases. Furthermore, the database D1 showing a correlation between the surface roughness R, apparent compressive stress Pr, and amount of wear K1 per unit frictional energy is created based on the acquired relationships shown in FIGS. 8, 9, and 10.

Figure 5:
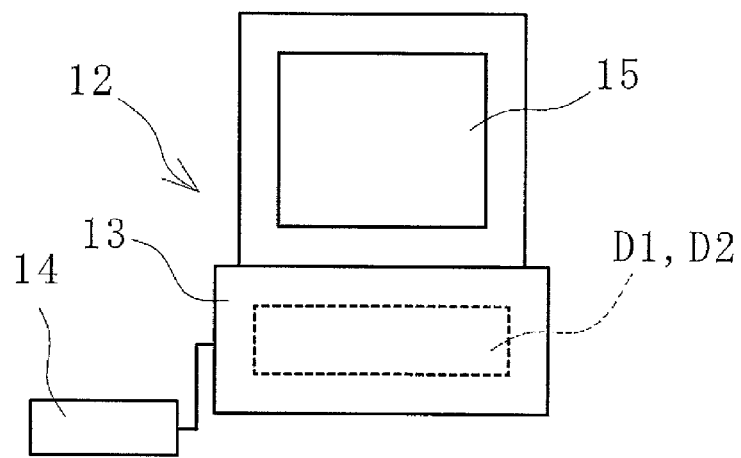
FIG. 5 is an explanatory diagram illustrating a system that recognizes a wear condition of a conveyor belt.

In order to recognize a wear condition of the upper cover rubber 3 of the conveyor belt 1 at a use site using the database D1, the apparent compressive stress Pr generated by a pressing force provided by the object to be conveyed C with regard to the upper cover rubber 3 at a use site is input into the calculation unit 13 from the input unit 14 illustrated in FIG. 5. Other already known data is preferably input in advance in the calculation unit 13. The calculation unit 13 displays on the display unit 15 a wear condition of the upper cover rubber 3 based on the database D1 and input apparent compressive stress Pr. A wear condition of the upper cover rubber 3 can be recognized by viewing the details displayed on the display unit 15.

For example, when recognizing a wear condition of the upper cover rubber 3 of a certain conveyor belt 1, the apparent compressive stress Pr generated on the upper cover rubber 3 at a use site is acquired and then input into the calculation unit 13. The conditions of the use site of the conveyor belt 1 is already known, and therefore, the apparent compressive stress Pr can be acquired by calculating from the already known conditions.

Figure 10:
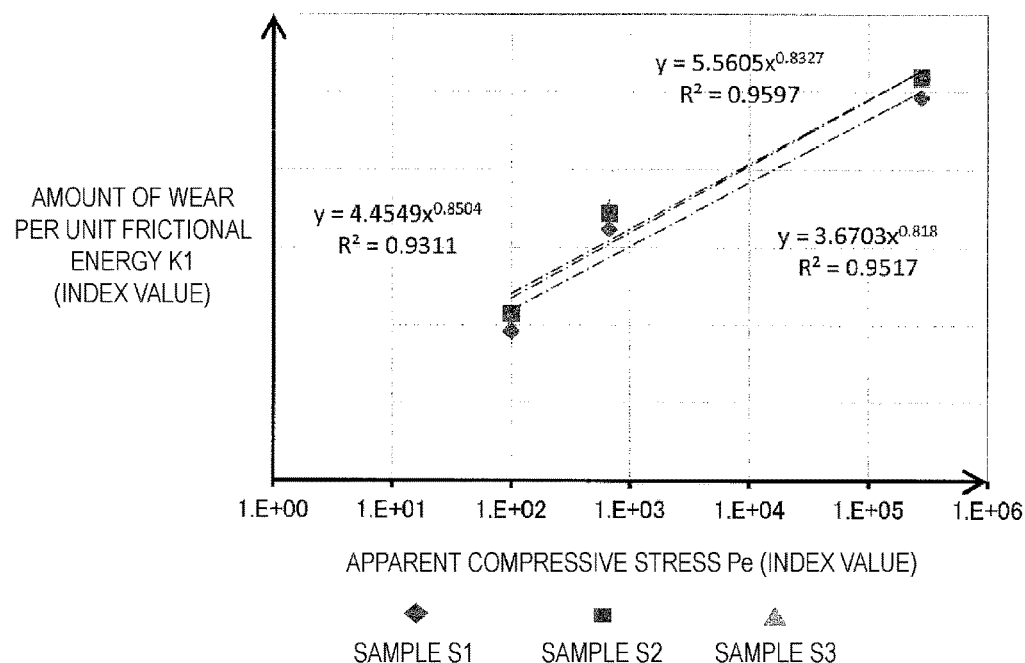
FIG. 10 is a graph showing a relationship between apparent compressive stress generated on a sample and amount of wear per unit frictional energy.

Next, in the data shown in FIG. 10, the wear amount of wear K1 per unit frictional energy of the upper cover rubber 3 is calculated by substituting the index value of the apparent compressive stress Pr generated on the upper cover rubber 3 for the apparent compressive stress Pe, using data for the same type of rubber as the upper cover rubber 3. The calculated amount of wear K1 per unit frictional energy is calculated based on the aforementioned equation, and therefore, an actual amount of wear X of the upper cover rubber 3 at a use site can be calculated based on the amount of wear K1 and the contact area Ar between the upper cover rubber 3 and object to be conveyed C at a use site. In other words, the amount of wear X of the upper cover rubber 3 can be displayed on the display unit 15 and recognized.

Alternatively, when recognizing the upper cover rubber 3 of a certain conveyor belt 1, the surface roughness R (Ra) of the upper cover rubber 3 at a use site is acquired and then input into the calculation unit 13. Next, in the data shown in FIG. 9, the wear amount of wear K1 per unit frictional energy of the upper cover rubber 3 is calculated by substituting the index value of the surface roughness Ra of the upper cover rubber 3 at a site for the surface roughness Ra, using data for the same type of rubber as the upper cover rubber 3. The calculated amount of wear K1 per unit frictional energy is calculated based on the aforementioned equation, and therefore, an amount of wear X of the upper cover rubber 3 at a use site can be calculated based on the amount of wear K1 and the contact area Ar between the upper cover rubber 3 and object to be conveyed C at a use site. Generally matching data is obtained for the calculated amount of wear X and the actual amount of wear X where the upper cover rubber 3 was actually measured.

In order to create the other database D2, a conventional wear resistance test is conducted using the sample S on a plurality of rubber types with different viscoelastic properties RRF (Rolling Resistance Factor). Furthermore, a relationship between the average wear pitch P calculated from the surface roughness R of the sample S obtained by the test and the viscoelastic properties RRF of the type or rubber of the sample S. The average wear pitch P is an interval of the wear lines L adjacent in the friction direction FD as illustrated in FIG. 6.

Figure 11:
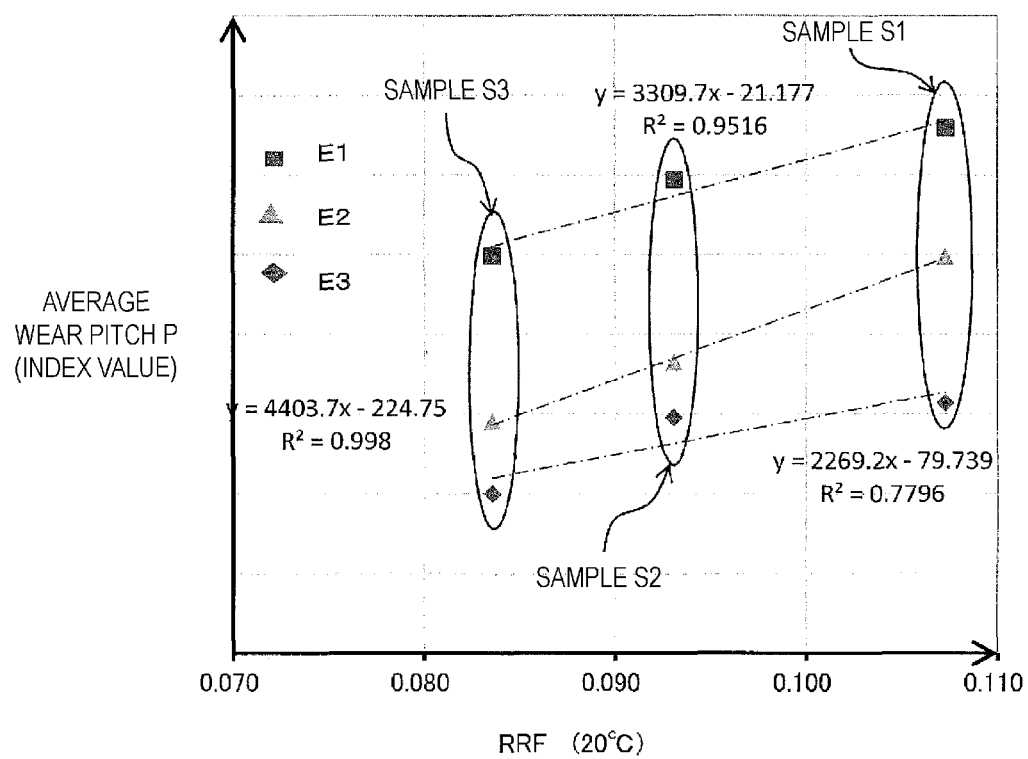
FIG. 11 is a graph showing a relationship between viscoelastic properties and average wear pitch of a sample.

The relationship between the average wear pitch P and the viscoelastic properties RRF has a high correlation as shown in FIG. 11. In FIG. 11, data obtained by performing three different types of wear resistance tests E1, E2, and E3 using three types of samples S1, S2, and S3 with different types of rubber are described. In FIG. 11, the average wear pitch P on a vertical axis is indicated by an index value, and as the index value increases, the average wear pitch P increases. Furthermore, RRF under a condition of 20° C. is used as the viscoelastic properties RRF on a horizontal axis in FIG. 11 is an indicator expressing dynamic visco-elasticity of rubber, and as the index value decreases, the rebound speed of the rubber increases, and response delay can be reduced, indicating that performance is excellent. The average wear pitch P varies based on the rubber type as shown in FIG. 11, and as the viscoelastic properties RRF of rubber increases, the average wear pitch P increases.

Figure 12:
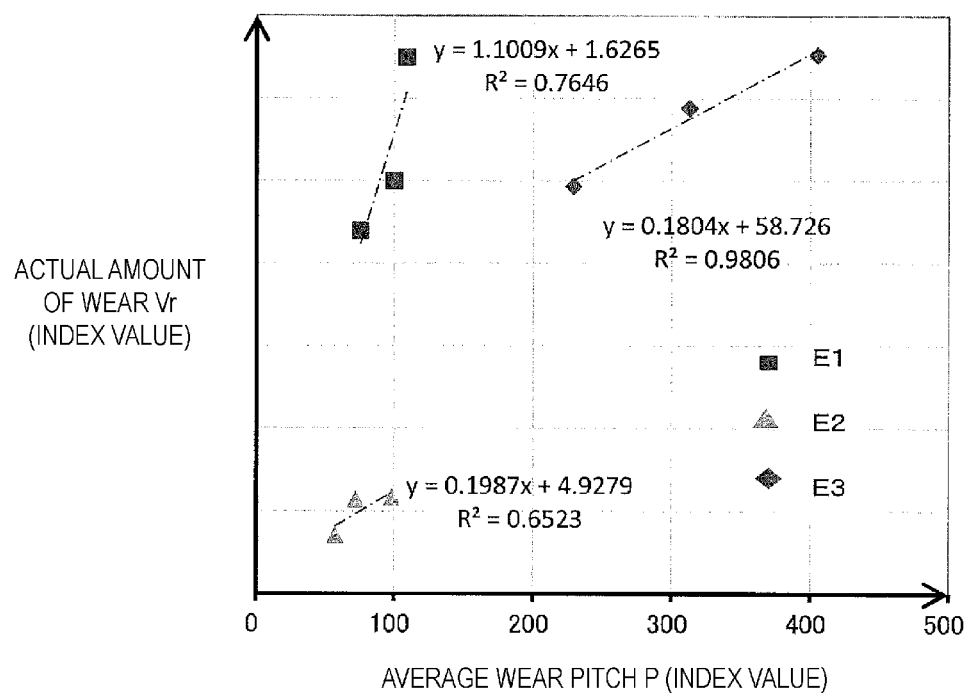
FIG. 12 is a graph showing a relationship between average wear pitch and actual amount of wear of a sample.

A relationship between the average wear pitch P and an actual amount of wear Vr of the sample S obtained by the test is further acquired by a conventional wear resistance test. The relationship between the average wear pitch P and actual amount of wear Vr has a high correlation as shown in FIG. 12, and as the average wear pitch P increases, the actual amount of wear Vr of the sample S increases. In FIG. 12, the actual amount of wear Vr on a vertical axis is indicated by an index value, and as the index value increases, the actual amount of wear Vr increases.

A relationship between the viscoelastic properties RRF and actual amount of wear Vr can be acquired based on the relationships shown in FIG. 11 and FIG. 12 acquired by the test. Furthermore, the database D2 showing a correlation between the average wear pitch P of the sample S, viscoelastic properties RRF, and actual amount of wear Vr is created based on the acquired relationships shown in FIGS. 11 and 12.

In order to recognize a wear condition of the upper cover rubber 3 of the conveyor belt 1 at a use site using the database D2, the rubber type (viscoelastic properties RRF) of the upper cover rubber 3 used in the conveyor belt 1 and the average wear pitch P of the upper cover rubber 3 at a use site are input in the calculation unit 13 from the input unit 14 illustrated in FIG. 5.

Next, in the data shown in FIG. 12, the amount of wear X of the upper cover rubber 3 is calculated by substituting the index value of the average wear pitch P of the upper cover rubber 3 at a use site for the average wear pitch P, using data for the same type of rubber (same viscoelastic properties RRF) as the upper cover rubber 3. In other words, the calculated amount of wear X of the upper cover rubber 3 can be displayed on the display unit 15 and recognized. Generally matching data is obtained for the calculated amount of wear X and the actual amount of wear X where the upper cover rubber 3 was actually measured.

Alternatively, the viscoelastic properties RRF or a rubber type used in the upper cover rubber 3 are input in the calculation unit 13 from the input unit 14 illustrated in FIG. 5. Furthermore, the extent of the average wear pitch P can be recognized based on the input viscoelastic properties RRF and the data in FIG. 11.

The database D1, D2 are stored in the calculation unit 13 in the embodiment, but in the present technology, one of the database D1, D2 may be stored in the calculation unit 13.

The invention claimed is:

1. A method of recognizing a conveyor belt wear condition, comprising the steps of:
   performing a rubber wear resistance test using a sample for each rubber type, by varying apparent compressive stress generated by a pressing force applied to the sample;
   acquiring a relationship between the apparent compressive stress and a surface roughness of the sample obtained from the test;
   acquiring a relationship between the surface roughness and an amount of wear per unit frictional energy of the sample obtained by the test;
   creating a database showing a correlation between the surface roughness, the apparent compressive stress, and the amount of wear per unit frictional energy based on the acquired relationships; and
   recognizing a wear condition of an upper cover rubber at a conveyor belt use site, based on the database and apparent compressive stress generated by a pressing force provided by an object to be conveyed with regard to the upper cover rubber.

2. The method of recognizing a conveyor belt wear condition according to claim 1, wherein an arithmetic mean roughness Ra is used as the surface roughness.

3. The method of recognizing a conveyor belt wear condition according to claim 1, wherein at least one of a DIN abrasion test and Pico abrasion test is used as the wear resistance test.

* * * * *